US008957952B2

(12) United States Patent
Tashiro et al.

(10) Patent No.: US 8,957,952 B2
(45) Date of Patent: Feb. 17, 2015

(54) COLOR SIGNAL TRANSMISSION DEVICE, WIRELESS IMAGE TRANSMISSION SYSTEM, AND TRANSMITTER

(71) Applicant: Olympus Medical Systems Corp., Tokyo (JP)

(72) Inventors: Junichi Tashiro, Tokyo (JP); Masashi Umemura, Tokyo (JP); Hideki Tashiro, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/922,730

(22) Filed: Jun. 20, 2013

(65) Prior Publication Data

US 2014/0002627 A1 Jan. 2, 2014

Related U.S. Application Data

(63) Continuation of application No. PCT/JP2012/078860, filed on Nov. 7, 2012.

(30) Foreign Application Priority Data

Nov. 11, 2011 (JP) ................................. 2011-247913

(51) Int. Cl.
*H04N 13/04* (2006.01)
*A61B 1/00* (2006.01)
(Continued)

(52) U.S. Cl.
CPC ............... *A61B 1/00016* (2013.01); *A61B 8/12* (2013.01); *H04N 7/173* (2013.01); *A61B 1/00006* (2013.01); *A61B 1/045* (2013.01); *A61B 8/56* (2013.01); *A61B 8/54* (2013.01)
USPC ................... 348/71; 348/70; 348/72; 348/73; 348/74; 348/75; 348/61; 348/62; 348/63; 348/64; 348/65

(58) Field of Classification Search
CPC .......... H04N 2005/2255; H04N 9/045; H04N 7/173; A61B 1/05; A61B 1/045; A61B 1/00009; A61B 1/00006; A61B 8/12; A61B 1/00193; G02B 21/27025; G02B 21/27027
USPC ................................................ 348/61–80, 45
See application file for complete search history.

(56) References Cited

U.S. PATENT DOCUMENTS 5,209,220 A   5/1993   Hiyama et al.
5,331,551 A   7/1994   Tsuruoka et al.
(Continued)

FOREIGN PATENT DOCUMENTS

JP   A-3-118025   5/1991
JP   A-3-121036   5/1991
(Continued)

OTHER PUBLICATIONS

Written Opinion of the International Searching Authority issued in International Patent Application No. PCT/JP2012/078860 dated Dec. 11, 2012 (w/ translation).

(Continued)

*Primary Examiner* — Andy Rao
*Assistant Examiner* — Shan Elahi
(74) *Attorney, Agent, or Firm* — Oliff PLC

(57) ABSTRACT

In a processor of a wireless image transmission system that transmits, by radio communication, an image signal obtained by converting an image obtained by an endoscope apparatus, a communication state detection unit monitors a communication state of radio communication. An editing unit edits the image signal according to a mode in which the endoscope apparatus obtains an image when the deterioration of a communication state is detected by the communication state detection unit. A transmission unit transmits the image signal output from the editing unit to a receiver.

8 Claims, 15 Drawing Sheets

(51) Int. Cl.
*A61B 8/12* (2006.01)
*H04N 7/173* (2011.01)
*A61B 1/045* (2006.01)
*A61B 8/00* (2006.01)

(56) References Cited

U.S. PATENT DOCUMENTS

| | | | |
|---|---|---|---|
| 5,408,263 A * | 4/1995 | Kikuchi et al. | 348/68 |
| 5,574,510 A * | 11/1996 | Abe | 348/584 |
| 7,235,775 B2 * | 6/2007 | Masaki | 250/226 |
| 7,450,571 B2 * | 11/2008 | Zhang et al. | 370/352 |
| 8,233,056 B2 * | 7/2012 | Harada et al. | 348/222.1 |
| 8,610,765 B2 * | 12/2013 | Yamaguchi | 348/73 |
| 8,836,795 B2 * | 9/2014 | Nagamune | 348/164 |
| 2001/0043786 A1 * | 11/2001 | Takahashi et al. | 386/46 |
| 2001/0052930 A1 * | 12/2001 | Adair et al. | 348/65 |
| 2002/0010938 A1 * | 1/2002 | Zhang et al. | 725/95 |
| 2003/0216626 A1 * | 11/2003 | Tsujita et al. | 600/321 |
| 2003/0228882 A1 * | 12/2003 | Ezumi | 455/550.1 |
| 2004/0019253 A1 * | 1/2004 | Tsujita et al. | 600/118 |
| 2005/0133690 A1 * | 6/2005 | Higashitsutsumi | 250/208.1 |
| 2005/0155080 A1 * | 7/2005 | Zhang et al. | 725/126 |
| 2005/0203343 A1 * | 9/2005 | Kang et al. | 600/160 |
| 2005/0215859 A1 * | 9/2005 | Chin et al. | 600/146 |
| 2006/0022234 A1 * | 2/2006 | Adair et al. | 257/292 |
| 2006/0071156 A1 * | 4/2006 | Masaki | 250/226 |
| 2006/0156201 A1 * | 7/2006 | Zhang et al. | 714/776 |
| 2006/0217594 A1 * | 9/2006 | Ferguson | 600/175 |
| 2007/0073154 A1 * | 3/2007 | Karasawa | 600/459 |
| 2008/0018733 A1 * | 1/2008 | Hasegawa | 348/68 |
| 2008/0114247 A1 * | 5/2008 | Urbano et al. | 600/447 |
| 2008/0177140 A1 * | 7/2008 | Cline et al. | 600/112 |
| 2008/0242931 A1 * | 10/2008 | Nishino | 600/117 |
| 2010/0289893 A1 * | 11/2010 | Yoo et al. | 348/135 |
| 2010/0312109 A1 * | 12/2010 | Satoh | 600/441 |
| 2011/0063427 A1 * | 3/2011 | Fengler et al. | 348/65 |
| 2012/0127294 A1 * | 5/2012 | Yamaguchi | 348/73 |
| 2012/0212619 A1 * | 8/2012 | Nagamune | 348/164 |
| 2012/0241620 A1 * | 9/2012 | On | 250/338.1 |

FOREIGN PATENT DOCUMENTS

| | | |
|---|---|---|
| JP | A-2005-58576 | 3/2005 |
| JP | A-2006-122586 | 5/2006 |
| JP | A-2008-23101 | 2/2008 |
| JP | A-2009-172280 | 8/2009 |
| JP | A-2011-41758 | 3/2011 |

OTHER PUBLICATIONS

International Search Report issued in International Patent Application No. PCT/JP2012/078860 dated Dec. 11, 2012.

* cited by examiner

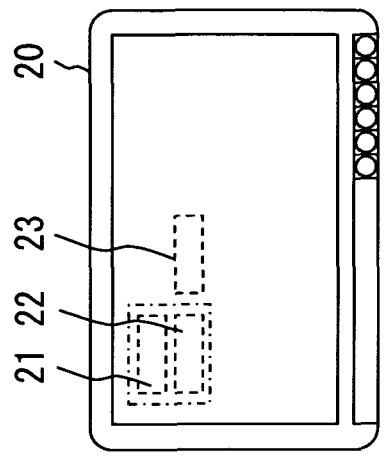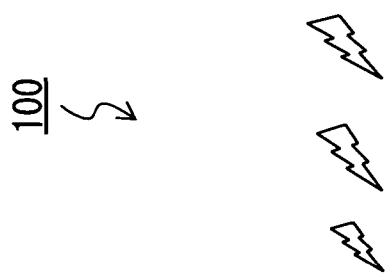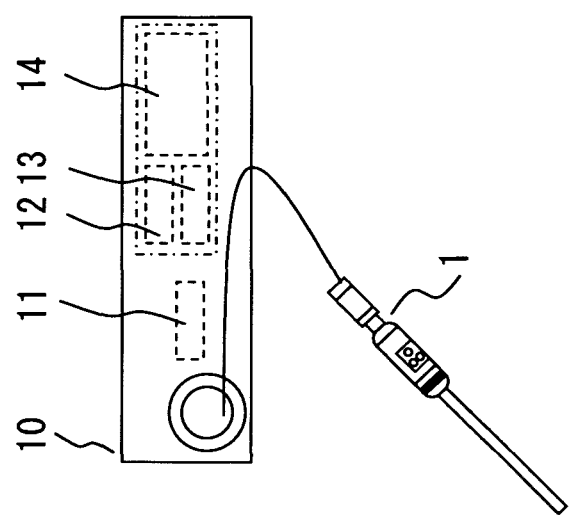
FIG. 1

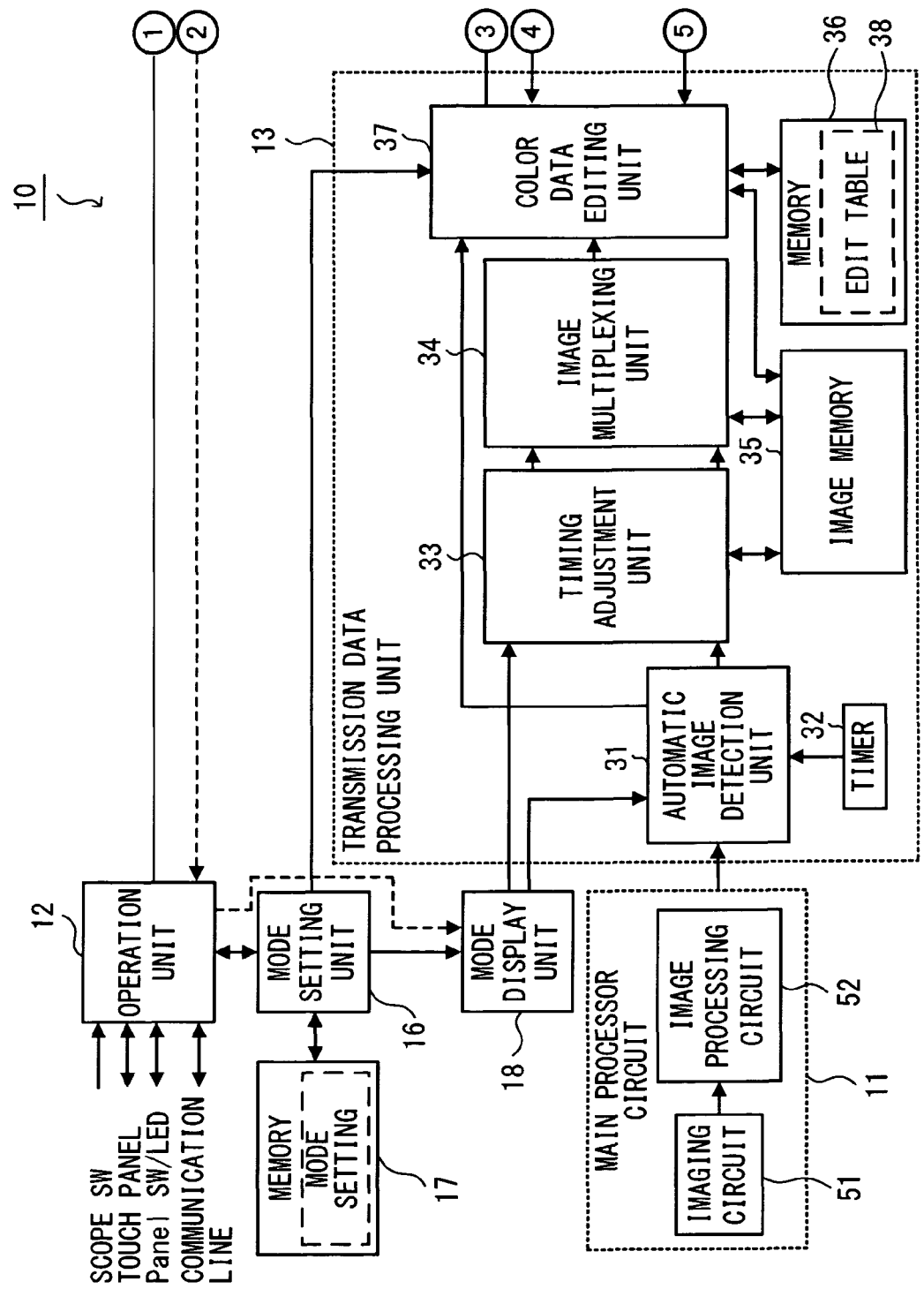
F I G. 2A

F I G. 4
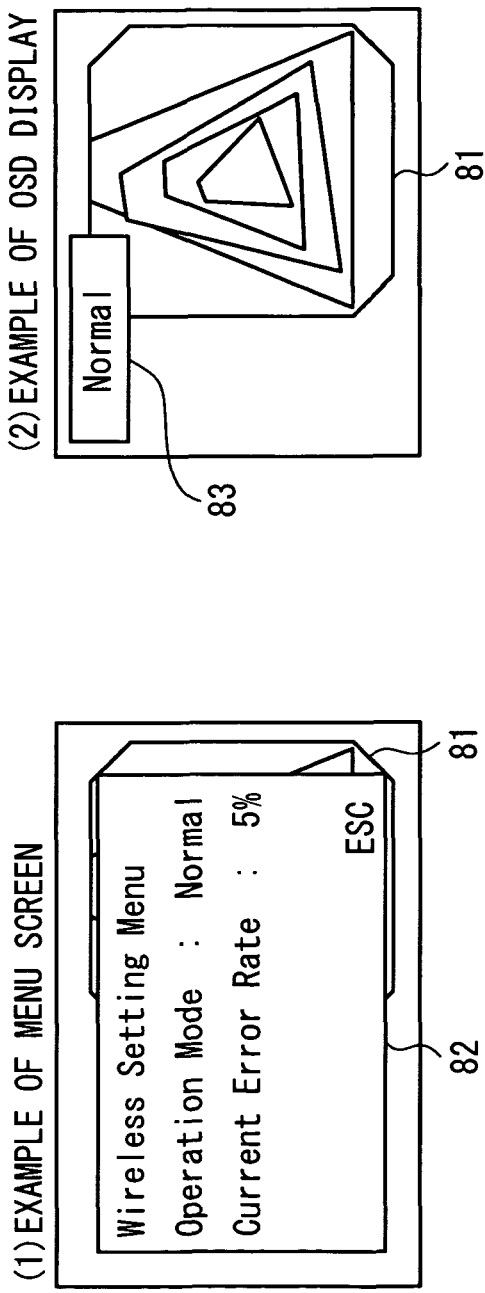

EXAMPLE OF PACKET INCLUDING ERROR RATE

| STX | Error Rate | Check Code | ETX |

STX       : CODE INDICATING FRONT DATA
Error Rate : DATA INDICATING ERROR RATE   00h:0%, 32h:50%, 4Bh:75%
Check Code : CODE FOR CHECKING TRANSMISSION ERROR SUCH AS CHECKSUM AND CRC CODE
ETX       : CODE INDICATING END OF DATA

EXAMPLE OF SIGNAL THAT IS OUTPUT TO IMAGE TRANSMITTER IN NORMAL MODE

| ERROR RATE | (1) MODIFIED VIDEO SIGNAL a (ENDOSCOPIC IMAGE) REDUCTION IN NUMBER OF BITS | (2) FORMAT INFORMATION |
|---|---|---|
| 0% | Y100%(10bit), Pb100%(10bit), Pr100%(10bit) | Y 100%, Pb100%, Pr100% |
| 50% | Y80%(8bit), Pb25%(2.5bit), Pr45%(4.5bit) | Y 80%, Pb25%, Pr45% |
| 75% | Y50%(5bit), Pb10%(1bit), Pr15%(1.5bit) | Y 50%, Pb10%, Pr15% |

DATA CONFIGURATION OF FORMAT INFORMATION

| Operation Mode | Y data length | Pb data length | Pr data length |
|---|---|---|---|

Operation Mode: 00h: NORMAL MODE, 01h: NBI MODE, 02h: ULTRASONIC MODE
Y data length : DATA LENGTH OF Y DATA (RATIO) 00h:100%, 32h:50%, 4Bh:25%
Pb data length: DATA LENGTH OF Pb DATA (RATIO)  SAME AS ABOVE
Pr data length: DATA LENGTH OF Pr DATA (RATIO)  SAME AS ABOVE

REDUCTION IN NUMBER OF PIXELS

NORMAL MODE 0% (Y100%, Pb100%, Pr100%)

| PIXEL NUMBER | 1 | 2 | 3 | 4 | 5 | 6 | 7 | 8 | 9 | 10 | 11 | 12 | 13 | 14 | 15 | 16 | 17 | 18 | 19 | 20 | ... |
|---|---|---|---|---|---|---|---|---|---|---|---|---|---|---|---|---|---|---|---|---|---|
| | Y Pb Pr | Y Pb Pr | Y Pb Pr | Y Pb Pr | Y Pb Pr | Y Pb Pr | Y Pb Pr | Y Pb Pr | Y Pb Pr | Y Pb Pr | Y Pb Pr | Y Pb Pr | Y Pb Pr | Y Pb Pr | Y Pb Pr | Y Pb Pr | Y Pb Pr | Y Pb Pr | Y Pb Pr | Y Pb Pr | .. |

NORMAL MODE 50% (Y80%, Pb25%, Pr45%)

| PIXEL NUMBER | 1 | 2 | 3 | 4 | 5 | 6 | 7 | 8 | 9 | 10 | 11 | 12 | 13 | 14 | 15 | 16 | 17 | 18 | 19 | 20 | ... |
|---|---|---|---|---|---|---|---|---|---|---|---|---|---|---|---|---|---|---|---|---|---|
| | Y Pb Pr | Y | Y Pr | Y | Y Pb Pr | Y | Y Pr | Y | Y Pb Pr | Y | Y Pr | Y | Y Pb Pr | Y | Y Pr | Y | Y Pb Pr | Y | Y | Y | .. |

NORMAL MODE 75% (Y50%, Pb10%, Pr15%)

| PIXEL NUMBER | 1 | 2 | 3 | 4 | 5 | 6 | 7 | 8 | 9 | 10 | 11 | 12 | 13 | 14 | 15 | 16 | 17 | 18 | 19 | 20 | ... |
|---|---|---|---|---|---|---|---|---|---|---|---|---|---|---|---|---|---|---|---|---|---|
| | Y Pb Pr | Y | Y | Y | Y | Y | Y | Y | Y | Y Pb Pr | Y | Y | Y | Y | Y | Y | Y | Y | Y Pr | Y | .. |

FIG. 9A

EXAMPLE OF SIGNAL THAT IS OUTPUT TO IMAGE TRANSMITTER IN NORMAL MODE

| ERROR RATE | (1) MODIFIED VIDEO SIGNAL b (ENDOSCOPIC IMAGE) REDUCTION IN NUMBER OF PIXELS | (2) FORMAT INFORMATION |
|---|---|---|
| 0% | | Y 100%, Pb100%, Pr100% |
| 50% | Y80% (1 PIXEL OUT OF 5 PIXELS IS REDUCED) Pb25% (3 PIXELS OUT OF 4 PIXELS ARE REDUCED) Pr45 (11 PIXELS OUT OF 20 PIXELS ARE REDUCED) | Y 80%, Pb25%, Pr45% |
| 75% | Y50% (1 PIXEL OUT OF 2 PIXELS IS REDUCED) Pb10% (9 PIXELS OUT OF 10 PIXELS ARE REDUCED) Pr15 (17 PIXELS OUT OF 20 PIXELS ARE REDUCED) | Y 50%, Pb10%, Pr15% |

FIG. 9B

DATA CONFIGURATION OF FORMAT INFORMATION

| Operation Mode | Y data length | Pb data length | Pr data length |
|---|---|---|---|

Operation Mode: 00h: NORMAL MODE, 01h: NBI MODE, 02h: ULTRASONIC MODE
Y data length : DATA LENGTH OF Y DATA (RATIO) 00h:100%, 32h:50%, 4Bh:25%
Pb data length: DATA LENGTH OF Pb DATA (RATIO)   SAME AS ABOVE
Pr data length: DATA LENGTH OF Pr data (RATIO)   SAME AS ABOVE

EXAMPLE OF SIGNAL THAT IS OUTPUT TO MAIN MONITOR CIRCUIT IN NORMAL MODE

| ERROR RATE | (1) INPUT VIDEO SIGNAL (ENDOSCOPIC IMAGE) | (2) INPUT FORMAT INFORMATION | (3) OUTPUT FORMAT INFORMATION |
|---|---|---|---|
| 0% | Y100%(10bit), Pb100%(10bit), Pr100%(10bit) | Y 100%, Pb100%, Pr100% | Y100%(10bit), Pb100%(10bit) Pr100%(10bit) |
| 50% | a: Y80%(8bit), Pb25%(2.5bit), Pr45%(4.5bit) | Y 80%, Pb25%, Pr45% | ※COMPRESSED BITS ARE INTERPOLATED. (e.g., FILLED WITH "0") |
|  | b: Y80% (1 PIXEL OUT OF 5 PIXELS IS REDUCED) Pb25% (3 PIXELS OUT OF 4 PIXELS ARE REDUCED) Pr45 (11 PIXELS OUT OF 20 PIXELS ARE REDUCED) |  | ※COMPRESSED BITS ARE INTERPOLATED. <1> PREVIOUS PIXEL IS COPIED <2> FILLED WITH SPECIFIC VALUE (e.g., "0") |
| 75% | a: Y50%(5bit), Pb10%(1bit), Pr15%(1.5bit) | Y 50%, Pb10%, Pr15% |  |
|  | b: Y50% (1 PIXEL OUT OF 2 PIXELS IS REDUCED) Pb10% (9 PIXELS OUT OF 10 PIXELS ARE REDUCED) Pr15 (17 PIXELS OUT OF 20 PIXELS ARE REDUCED) |  |  |

F I G. 1 0

| SET MODE | TRIGGER CONDITION |
|---|---|
| NORMAL MODE | OTHER THAN THE BELOW |
| NBI MODE | COLOR COMPONENT OF Pb IS N OR MORE TIMES GREATER THAN Pr ("N" MAY BE ANY VALUE) |
| ULTRASONIC MODE | CASES IN WHICH THERE IS NO COLOR INFORMATION OF Pb AND Pr |

FIG. 11

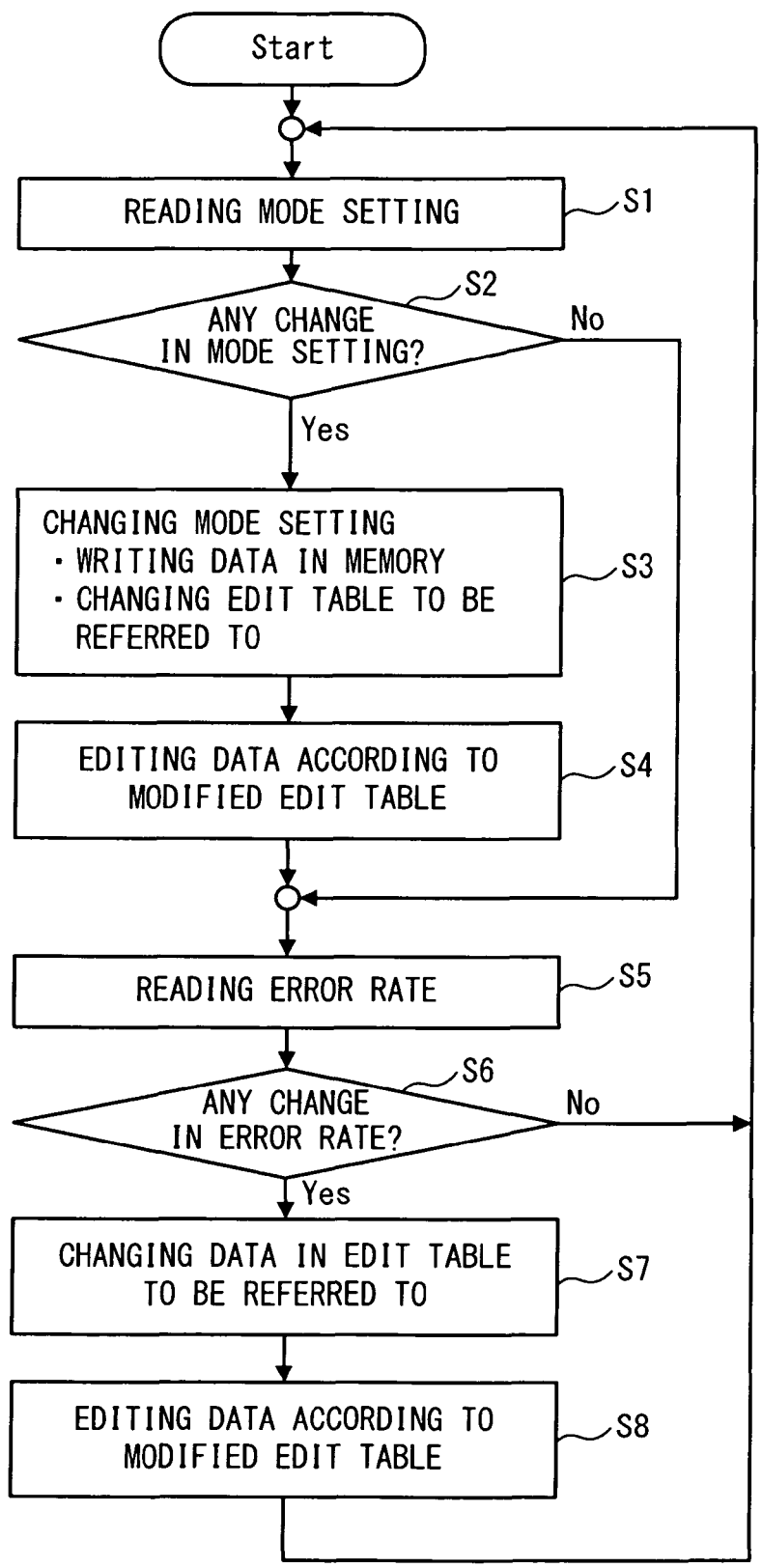
F I G. 1 2

US 8,957,952 B2

COLOR SIGNAL TRANSMISSION DEVICE, WIRELESS IMAGE TRANSMISSION SYSTEM, AND TRANSMITTER

CROSS-REFERENCE TO RELATED APPLICATIONS

This application is based upon and claims the benefit of priority of the prior Japanese Patent Application No. 2011-247913, filed Nov. 11, 2011, the entire contents of which are incorporated herein by reference.

This is a Continuation Application of PCT Application No. PCT/JP2012/078860, filed Nov. 7, 2012, which was not published under PCT Article 21(2) in English.

FIELD

The present invention relates to a color signal transmission device, a wireless image transmission system, and a transmitter for transmitting an image from a transmitter to a receiver.

BACKGROUND

A wireless endoscope system that transmits and receives an image signal by radio is known in the art to replace a conventionally used endoscope system by which an endoscopic image or the like is transmitted through an image cable and is displayed on a monitor.

A wireless endoscope system has a characteristic that an image signal is transmitted by radio communication, and thus the traffic or communication rate may drop as affected by disturbance, noise or the like. For the purposes of compensating for the above, conventionally, a frame rate is changed or an image is compressed by reducing some color data of the image in order to maintain the communication, as disclosed in Japanese Laid-open Patent Publication No. 2009-172280 or Japanese Laid-open Patent Publication No. 2006-122586.

Japanese Laid-open Patent Publication No. 2011-041758 discloses a technique by which normal light observation and special light observation can be performed, as a known technique in the art related to a medical endoscope apparatus.

SUMMARY

A color signal transmission device according to one aspect of the present invention includes: a first color signal generation unit to generate a first color signal from among a plurality of color signals for creating an image; a second color signal generation unit to generate a second color signal from among a plurality of color signals for creating an image; a diagnostic mode selection unit capable of selecting either a first diagnostic mode for creating a first diagnostic image by using the first color signal and the second color signal, or a second diagnostic mode for creating a second diagnostic image that is different from the first diagnostic mode; a priority determination unit to determine superiority of information among color signals generated by the first color signal generation unit and the second color signal generation unit, according to a diagnostic mode selected by the diagnostic mode selection unit; a transmission rate changing unit to change transmission rates of the first color signal generated by the first color signal generation unit and the second color signal generated by the second color signal generation unit, according to a priority determined by the priority determination unit; and a color signal transmission unit to transmit the first color signal and the second color signal according to a transmission rate changed by the transmission rate changing unit, wherein when a special light mode in which endoscopy with special light is performed is selected by the diagnostic mode selection unit, the transmission rate changing unit changes transmission rates of the first and second color signals such that a ratio of a Pb component of an image signal becomes higher than that of a Pr component.

A color signal transmission device according to another aspect of the present invention includes: a first color signal generation unit to generate a first color signal from among a plurality of color signals for creating an image; a second color signal generation unit to generate a second color signal from among a plurality of color signals for creating an image; a diagnostic mode selection unit capable of selecting either a first diagnostic mode for creating a first diagnostic image by using the first color signal and the second color signal, or a second diagnostic mode for creating a second diagnostic image that is different from the first diagnostic mode; a priority determination unit to determine superiority of information among color signals generated by the first color signal generation unit and the second color signal generation unit, according to a diagnostic mode selected by the diagnostic mode selection unit; a transmission rate changing unit to change transmission rates of the first color signal generated by the first color signal generation unit and the second color signal generated by the second color signal generation unit, according to a priority determined by the priority determination unit; and a color signal transmission unit to transmit the first color signal and the second color signal according to a transmission rate changed by the transmission rate changing unit, wherein when an ultrasonic mode in which endoscopy with ultrasonic waves is performed is selected by the diagnostic mode selection unit, the transmission rate changing unit changes transmission rates of the first and second color signals such that a ratio of a Y component of an image signal becomes high.

A transmitter according to one aspect of the present invention is used in a wireless image transmission system that transmits and receives, by radio communication, an image signal obtained by converting an image that is obtained by an endoscope apparatus, and the transmitter includes: a communication state detection unit to monitor a communication state of radio communication; an editing unit to edit the image signal according to a mode in which the endoscope apparatus obtains an image when a change in a communication state is detected by the communication state detection unit; a transmission unit to transmit the image signal output from the editing unit to a receiver; a mode determination unit to determine a mode that is set to the endoscope apparatus from among a normal mode in which normal endoscopy is performed, a special light mode in which endoscopy with special light is performed, and an ultrasonic mode in which endoscopy with ultrasonic waves is performed; and a storage unit to store color data reduction rate information in each of the normal mode, the special light mode, and the ultrasonic mode, wherein when the image signal is to be edited, the editing unit obtains color data reduction rate information that corresponds to a mode determined by the mode determination unit from the storage unit, and edits a ratio of color data according to the obtained color data reduction rate information, and when the communication state detection unit detects deterioration in a communication state and the mode is the special light mode, the editing unit edits the image signal such that a ratio of a Pb component becomes higher than that of a Pr component.

A transmitter according to another aspect of the present invention is used in a wireless image transmission system that transmits and receives, by radio communication, an image signal obtained by converting an image that is obtained by an endoscope apparatus, and the transmitter includes: a communication state detection unit to monitor a communication state of radio communication; an editing unit to edit the image signal according to a mode in which the endoscope apparatus obtains an image when a change in a communication state is detected by the communication state detection unit; a transmission unit to transmit the image signal output from the editing unit to a receiver; a mode determination unit to determine a mode that is set to the endoscope apparatus from among a normal mode in which normal endoscopy is performed, a special light mode in which endoscopy with special light is performed, and an ultrasonic mode in which endoscopy with ultrasonic waves is performed; and a storage unit to store color data reduction rate information in each of the normal mode, the special light mode, and the ultrasonic mode, wherein when the image signal is to be edited, the editing unit obtains color data reduction rate information that corresponds to a mode determined by the mode determination unit from the storage unit, and edits a ratio of color data according to the obtained color data reduction rate information, and when the communication state detection unit detects deterioration in a communication state and the mode is the ultrasonic mode, the editing unit edits the image signal such that a ratio of a Y component becomes high.

A wireless image transmission system according to one aspect of the present invention includes a transmitter to transmit, by radio communication, an image signal obtained by converting an image that is obtained by an endoscope apparatus, and a receiver having a display unit on which the image signal received from the transmitter is displayed, the transmitter including: a communication state detection unit to monitor a communication state of radio communication; an editing unit to edit the image signal according to a mode in which the endoscope apparatus obtains an image when a change in a communication state is detected by the communication state detection unit; a transmission unit to transmit the image signal output from the editing unit to a receiver; a mode determination unit to determine a mode that is set to the endoscope apparatus from among a normal mode in which normal endoscopy is performed, a special light mode in which endoscopy with special light is performed, and an ultrasonic mode in which endoscopy with ultrasonic waves is performed; and a storage unit to store color data reduction rate information in each of the normal mode, the special light mode, and the ultrasonic mode, and the receiver including an analysis unit to edit an image signal received from the transmitter into a format enabling the image signal to be displayed on the display unit, and to detect a communication state, wherein when the image signal is to be edited, the editing unit obtains color data reduction rate information that corresponds to a mode determined by the mode determination unit from the storage unit, and edits a ratio of color data according to the obtained color data reduction rate information, and when the communication state detection unit detects deterioration in a communication state and the mode is the special light mode, the editing unit edits the image signal such that a ratio of a Pb component becomes higher than that of a Pr component.

A wireless image transmission system according to another aspect of the present invention includes a transmitter to transmit, by radio communication, an image signal obtained by converting an image that is obtained by an endoscope apparatus, and a receiver having a display unit on which the image signal received from the transmitter is displayed, the transmitter including: a communication state detection unit to monitor a communication state of radio communication; an editing unit to edit the image signal according to a mode in which the endoscope apparatus obtains an image when a change in a communication state is detected by the communication state detection unit; a transmission unit to transmit the image signal output from the editing unit to a receiver; a mode determination unit to determine a mode that is set to the endoscope apparatus from among a normal mode in which normal endoscopy is performed, a special light mode in which endoscopy with special light is performed, and an ultrasonic mode in which endoscopy with ultrasonic waves is performed; and a storage unit to store color data reduction rate information in each of the normal mode, the special light mode, and the ultrasonic mode, and the receiver including an analysis unit to edit an image signal received from the transmitter into a format enabling the image signal to be displayed on the display unit, and to detect a communication state, wherein when the image signal is to be edited, the editing unit obtains color data reduction rate information that corresponds to a mode determined by the mode determination unit from the storage unit, and edits a ratio of color data according to the obtained color data reduction rate information, and when the communication state detection unit detects deterioration in a communication state and the mode is the ultrasonic mode, the editing unit edits the image signal such that a ratio of a Y component becomes high.

BRIEF DESCRIPTION OF DRAWINGS

The present invention will be more apparent from the following detailed description when the accompanying drawings are referenced.

FIG. 1 is a block diagram of the entirety of a wireless image transmission system according to an embodiment.

FIG. 2A is a block diagram (part 1) of a processor according to an embodiment.

FIG. 4 illustrates how a diagnostic mode is set.

FIG. 5 illustrates an example of the format of a packet notifying an error rate.

FIGS. 7A and 7B depict an example of the signal that a processor transmits in the case where color data is edited according to an edit table of FIG. 6.

FIG. 8 illustrates an example of the configuration of an edit table of color data, which is used when the method achieved by reducing the number of pixels is adopted.

FIGS. 9A and 9B depict an example of the signal that a processor transmits in the case where the color data is edited according to the edit table of FIG. 8.

FIG. 10 depicts processes in which color data of the signal received from a processor is interpolated by a monitor and the signal is output.

FIG. 11 depicts an example of how an automatic image detection unit recognizes a diagnostic mode from the color information of image.

FIG. 12 is a flowchart of a color data editing process performed by a color data editing unit.

DESCRIPTION OF EMBODIMENTS

Figure 2B:
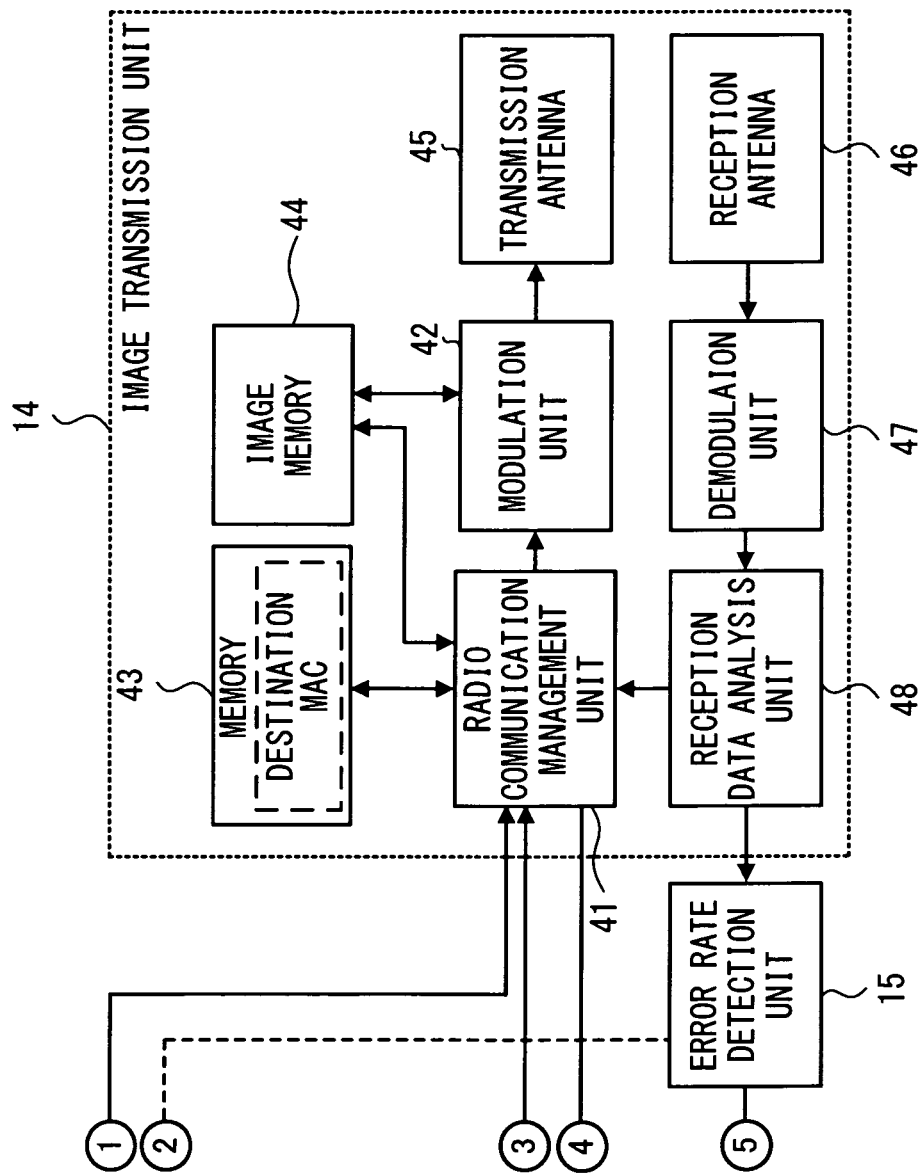
FIG. 2B is a block diagram (part 2) of a processor according to an embodiment.

Some embodiments of the present invention will be described in detail with reference to the drawings.

FIG. 1 is a block diagram of the entirety of a wireless image transmission system according to the present embodiment. A wireless image transmission system 100 of FIG. 1 includes a processor 10 and a monitor 20, and the processor 10 and the monitor 20 exchanges an image signal with each other by radio communication. In FIG. 1, the configuration related to a method for transmitting and receiving an image signal according to the present embodiment is illustrated, and the configurations in other respects are omitted.

The processor 10 includes a main processor circuit 11, an operation unit 12, a transmission data processing unit 13 and an image transmission unit 14, and the processor 10 performs image processing on the endoscopic images obtained by an endoscope 1. The operation unit 12, the transmission data processing unit 13, and the image transmission unit 14 in the configuration of the processor 10 may be installed in a processor, or may be installed as an external unit. The configuration of each element of the processor 10 will be described later in detail with reference to FIGS. 2A and 2B and the like.

The monitor 20 includes an image reception unit 21, an operation unit 22 and a main monitor circuit 23, and the monitor 20 displays the image signal received from the processor 10 on a display unit. The image reception unit 21 and the operation unit 22 in the configuration of the monitor 20 may be installed in the monitor 20, or may be installed as an external unit. The configuration of each element of the monitor 20 will be described later in detail with reference to FIG. 3 and the like.

When a deterioration or the like is detected in the state of radio communication while an endoscopic image is being transmitted by radio communication from the processor 10 to the monitor 20, the wireless image transmission system 100 of FIG. 1 edits the color data of an image signal according to a communication state and the characteristics of an endoscopic image that is being transmitted. The wireless image transmission system 100 controls the amount of data to be transmitted or received according to the state of radio communication, and continues the transmission of an image signal.

The configuration and operation of each element of the processor 10 and the monitor 20 of the wireless image transmission system 100 according to the present embodiment will be described below in detail.

FIGS. 2A and 2B are block diagrams of a processor according to the present embodiment. The processor 10 of FIGS. 2A and 2B includes the operation unit 12, a mode setting unit 16, a mode display unit 18, memory 17, the main processor circuit 11, the transmission data processing unit 13, the image transmission unit 14 and an error rate detection unit 15.

The main processor circuit 11 of the processor 10 includes an imaging circuit 51 and an image processing circuit 52. The main processor circuit 11 uses the image processing circuit 52 to perform image processing on the endoscopic images input from the imaging circuit 51 that is arranged at the tip of the inserting part of the endoscope 1. The main processor circuit 11 has a color signal generation unit that generates a color signal for each one of a plurality of color signals for generating an image.

The operation unit 12 accepts various settings of a radio communication or diagnostic mode according to the input operation performed by a user of the wireless image transmission system 100, and the operation unit 12 displays the setting or communication state. The diagnostic mode indicates the kind of the image output from the main processor circuit 11 of FIGS. 2A and 2B, and includes, for example, a normal mode in which a normal endoscopic observation image is displayed, an NBI (Narrow Band Imaging) mode (special light mode) in which a narrow bandwidth light observation image is displayed, and an ultrasonic mode in which an ultrasonic wave observation image is displayed. The various settings of a radio communication or diagnostic mode are achieved, for example, by receiving an input from a scope switch, a touch panel on the main body of the processor 10, a panel switch and LED (Light Emitting Diode) display on the main body of the processor 10 in a similar manner to touch panel on the main body of the processor 10, and from an external device via a serial communication. Note that the scope switch is arranged such that an operator who performs an endoscopic surgery or the like by using the endoscope 1 will be able to perform a setting operation within a sterilized area.

The mode setting unit 16 stores the diagnostic mode set through the operation unit 12 in the memory 17, and instructs the mode display unit 18 to output and display the set diagnostic mode. The mode setting unit 16 also notifies the transmission data processing unit 13 of notification of the diagnostic mode provided by the operation unit 12.

The transmission data processing unit 13 processes image such as endoscopic images. In particular, when a communication state is deteriorated, the transmission data processing unit 13 edits the color data of image data according to the notification of the diagnostic mode provided by the mode setting unit 16.

The transmission data processing unit 13 includes an automatic image detection unit 31, a timer 32, a timing adjustment unit 33, an image multiplexing unit 34, image memory 35, memory 36 and a color data editing unit 37.

It may be configured such that the diagnostic mode will be automatically detected by the processor 10 via the operation unit 12. In such cases, the automatic image detection unit 31 of the transmission data processing unit 13 analyzes the image input from the main processor circuit 11, and determines a diagnostic mode. How a diagnostic mode is determined will be described later in detail with reference to FIG. 11. The automatic image detection unit 31 performs a chattering control by using the timer 32 such that a diagnostic mode will not be frequently changed due to an automatic detection process of a diagnostic mode.

The timing adjustment unit 33 synchronizes the image input from the main processor circuit 11 with the OSD (On-Screen Display) image input from the mode display unit 18.

The image multiplexing unit 34 multiplexes the image and the OSD image synchronized by the timing adjustment unit 33. The memory 35 of the transmission data processing unit 13 is used to store an image on a temporary basis for performing a multiplexing process.

When a communication state is deteriorated, the color data editing unit 37 refers to an edit table 38 of the memory 36, and edits, according to a diagnostic mode, the ratio of the color data of the image data that has been input from the main processor circuit 11 according to a communication state. Then, the color data editing unit 37 reduces the amount of data to be transmitted or received with the monitor 20. In the embodiment, the ratio of the color data is changed according to an error rate. In regard to the deterioration of a communication state, determination is made according to the notification provided by the error rate detection unit 15, as will be described later. When there are several diagnostic modes, the color data editing unit 37 edits the ratio of the color data according to a diagnostic mode, and outputs an image signal and the information indicating the edited ratio of the image signal to the image transmission unit 14. A specific example of how color data is edited will be described in detail with reference to FIG. 6, FIG. 8, and the like.

The image transmission unit 14 includes a radio communication management unit 41, a modulation unit 42, memory 43, image memory 44, a transmission antenna 45, a reception antenna 46, a demodulation unit 47, and a reception data analysis unit 48. The image transmission unit 14 performs a necessary process for an image signal whose color data is edited as necessary by the transmission data processing unit 13, and transmits the image signal by radio. Moreover, the image transmission unit 14 receives a radio signal related to the transmitted image signal from the monitor 20, and performs a necessary process for the received radio signal.

The radio communication management unit 41 manages the radio communication with the monitor 20 according to the communication system or the like set via the operation unit 12. In particular, the radio communication management unit 41 performs a wireless connection (link) process or a transaction (retransmission control) process. Information to be used for radio communication, for example, information such as the MAC address (Media Access Control address) of the monitor 20 to be connected with is stored in the memory 43.

In the embodiment, a radio modulation technique such as QAM (Quadrature Amplitude Modulation) or QPSK (Quadrature Phase Shift Keying), or a radio transmission system such as polarization technique or MIMO (Multiple Input Multiple Output) will not be specified. Any radio transmission system may be adopted. A method for avoiding an error in the event of a radio communication error includes frequency band modification, transmission system modification, retransmission control, or the like, but such an avoiding method is not specified herein and any method may be adopted.

The modulation unit 42 modulates the image signal input from the transmission data processing unit 13. The image memory 44 is used to store image when the modulation unit 42 performs a modulation process.

The transmission antenna 45 transmits the modulation signal input from the modulation unit 42 to the outside as a radio signal. As described above, an image signal of an endoscopic image is transmitted to the monitor 20 of FIG. 1. When a radio signal is received from the processor 10, the monitor 20 returns a packet that includes an error rate to the processor 10.

The reception antenna 46 receives the radio signal transmitted from the monitor 20 in the way described above.

The demodulation unit 47 demodulates the radio signal received at the reception antenna 46.

The reception data analysis unit 48 analyzes the received data obtained in the demodulation, and notifies each unit, such as the radio communication management unit 41 and the error rate detection unit 15 of required information, respectively. The information provided to the radio communication management unit 41 is required to maintain the radio communication with the monitor 20. This technique is well known in the art, and thus the detailed description is omitted herein. The error rate detection unit 15 is notified of the detected error rate.

The error rate detection unit 15 compares the notified error rate from the reception data analysis unit 48 of the image transmission unit 14 with a specified threshold, and determines whether or not to notify the color data editing unit 37 of the transmission data processing unit 13 of an error rate. When it is determined that the color data editing unit 37 be notified of an error rate, the error rate detection unit 15 provides notification to the color data editing unit 37. When the mode display unit 18 is capable of displaying a communication state such as an error rate, the error rate detection unit 15 may instruct the operation unit 12 to display the error rate on the mode display unit 18.

Figure 3:
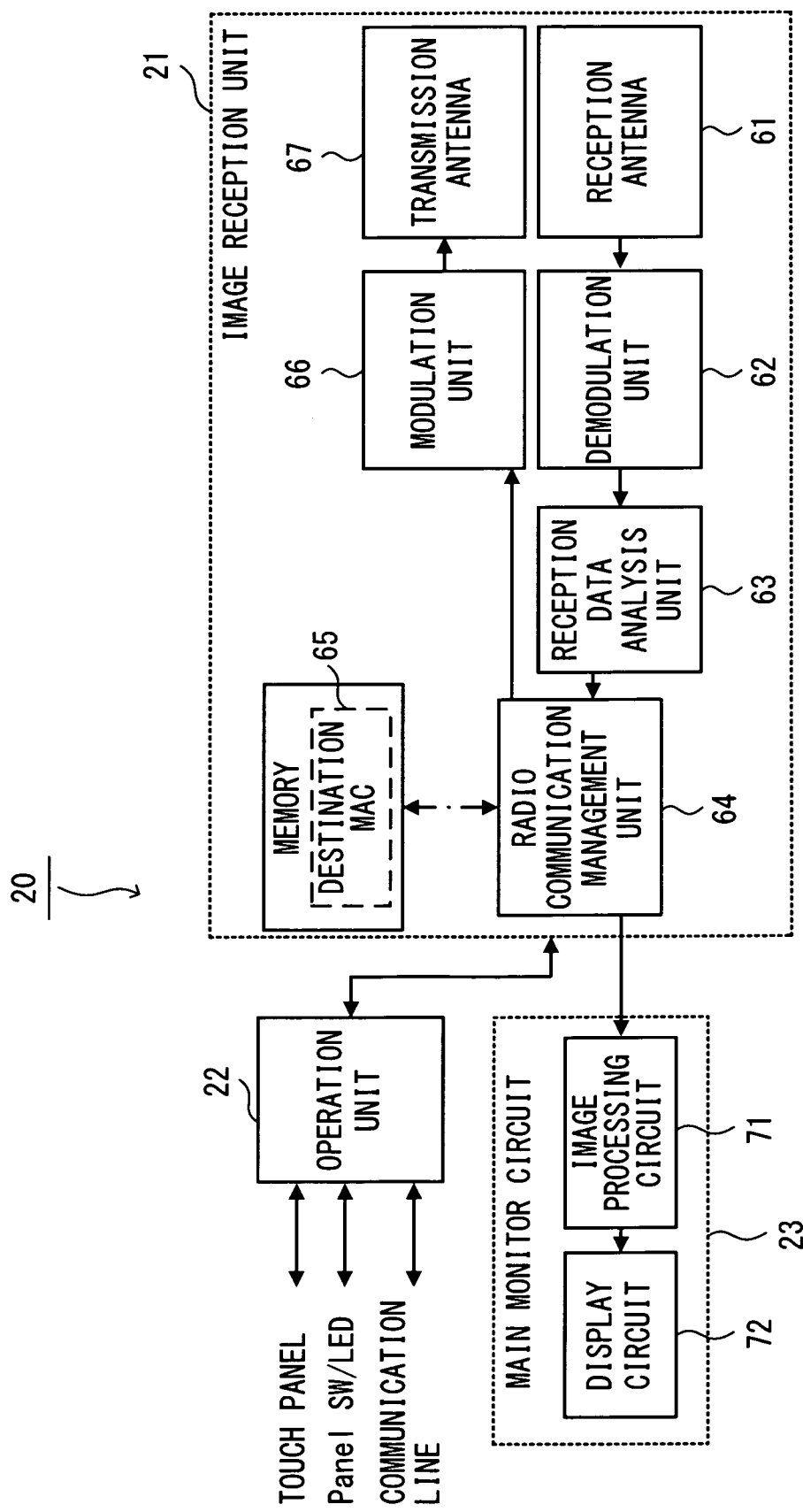
FIG. 3 is a block diagram of a monitor according to an embodiment.

FIG. 3 is a block diagram of a monitor according to the present embodiment. The monitor 20 of FIG. 3 includes the image reception unit 21, the main monitor circuit 23, and the operation unit 22. The monitor 20 receives the image signal transmitted from the processor 10 by radio communication, and displays an endoscopic image or the like on a screen.

The operation unit 22 accepts various settings of the radio communication with the processor 10 according to the input operation performed by a user of the wireless image transmission system 100, and displays the details of the settings. The various settings of a radio communication are performed, for example, by receiving an input from a touch panel on the main body of the monitor 20, a panel switch and LED display on the main body of the monitor 20 in a similar manner to the touch panel on the main body of the monitor 20, and from an external device via a serial communication.

The main monitor circuit 23 includes an image processing circuit 71 and a display circuit 72. The image processing circuit 71 performs image processing on the image signal received from the processor 10 through the image reception unit 21, and the display circuit 72 performs display on a screen.

The image reception unit 21 includes a reception antenna 61, a demodulation unit 62, a reception data analysis unit 63, a radio communication management unit 64, memory 65, a modulation unit 66, and a transmission antenna 67. The image reception unit 21 receives an image signal or the like from the processor 10 and performs a necessary process for the received image signal or the like, and performs a necessary process for a signal to be transmitted to the processor 10 and transmits the signal by radio.

The reception antenna 61 receives the radio signal transmitted from the processor 10 of FIGS. 2A and 2B.

The demodulation unit 62 demodulates the radio signal received at the reception antenna 61.

The reception data analysis unit 63 analyzes the data obtained in the demodulation, and calculates an error rate. The error rate is calculated, for example, by measuring a baud rate. The reception data analysis unit 63 also edits the image signal of the received signal to the image format that may be received by the main monitor circuit 23, and then outputs the signal to the main monitor circuit 23. How an image format is edited will be described with reference to FIG. 10.

The radio communication management unit 64 manages the radio communication with the processor 10 according to the communication system or the like that is set via the operation unit 22. In particular, the radio communication management unit 64 performs a wireless connection (link) process or a transaction (retransmission control) process. Information to be used for radio communication, for example, information such as the MAC address of the processor 10 to be connected with is stored in the memory 65.

The modulation unit 66 modulates a signal to be transmitted to the processor 10.

The transmission antenna 67 transmits the modulation signal input from the modulation unit 66 to the outside as a radio signal.

FIG. 4 illustrates how a diagnostic mode is set. As described above, when a diagnostic mode is designated by a user such as an operator through the operation unit 12 of the processor 10, the processor 10 stores the designated diagnostic mode in the memory 17.

As a technique in which a user sets a diagnostic mode, a setting menu 82 is superimposed on an endoscopic image 81 on a screen of the monitor 20, as illustrated in an example of the menu screen of (1) of FIG. 4. Alternatively, a diagnostic mode set to the endoscopic image 81 is OSD-displayed, as illustrated in an OSD display of (2) of FIG. 4 as an example. A user may set a diagnostic mode through a screen of the monitor 20 on which the endoscopic image 81 is displayed even when an endoscopic surgery or the like is being performed.

As described above, when a communication state is deteriorated while an endoscopic image is being transmitted by radio communication in the wireless image transmission system 100 according to the present embodiment, the processor 10 maintains the communication by reducing the amount of data accordingly and by changing the ratio of the color data of an image signal. The processor 10 from which an image signal is transmitted detects the deterioration of a communication state by referring to a packet indicating an error rate, which is transmitted from the monitor 20.

FIG. 5 illustrates an example of the format of a packet notifying an error rate. Data indicating an error rate is included in a specified field of the packet received by the processor 10 from the monitor 20. FIG. 5 illustrates an example of the case in which data indicating an error rate is stored in a field "Error Rate". In the example of FIG. 5, an error rate of 0 percent is indicated when data "00h" is stored, and an error rate of 50 percent and an error rate of 75 percent are indicated by data "32h" and data "4Bh", respectively.

In regard to the values to be stored in a field "Error Rate", some patterns may be prepared as illustrated in FIG. 5 as examples. In such cases, when the value of the error rate measured by the radio communication management unit 64 of the monitor 20 exceeds a prepared value, the maximum value from the prepared values is stored in a field, and notification is provided to the processor 10. Alternatively, it may be configured in such a manner that the value of the error rate measured by the radio communication management unit 64 of the monitor 20 is stored in a field without any change and notification is provided to the processor 10.

The reception data analysis unit 48 of the processor 10 notifies the error rate detection unit 15 of the value stored in the field "Error Rate" of the received packet. When the error rate in the notification exceeds a specified threshold, the error rate detection unit 15 notifies the color data editing unit 37 of the transmission data processing unit 13 of the error rate. In the embodiment, 50 percent and 75 percent are set as thresholds. The color data editing unit 37 determines a portion of the edit table 38 to be referred to according to the error rate notified from the error rate detection unit 15.

As described above, the processor 10 changes the ratio of the color data to be transmitted to the monitor 20 in accordance with a transmission rate. In the embodiment, when a plurality of diagnostic modes are prepared, the amount of data is reduced by changing the ratio of the color data in such a manner that the influence on the image quality of an endoscopic image is minimized according to a diagnostic mode, i.e., according to what sort of observation image the endoscopic image is. As a method for changing the ratio of the color data, firstly, there is a method achieved by reducing the number of bits, and secondly, there is another method achieved by reducing the number of pixels. Next, such methods for changing the ratio of the color data will be described in a specific manner with reference to FIGS. 6-9.

Figure 6:
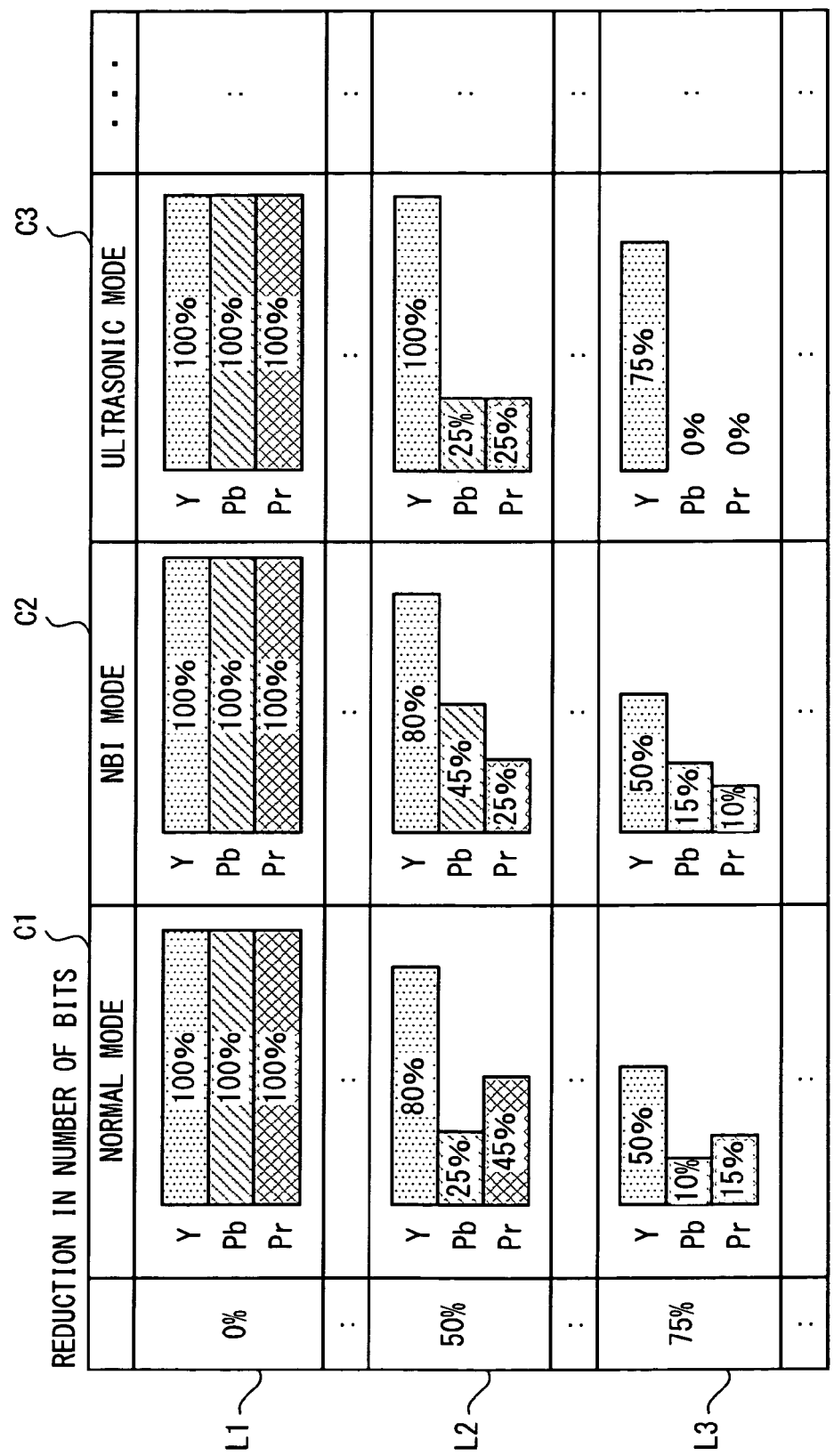
FIG. 6 illustrates an example of the configuration of an edit table of color data, which is used when the method achieved by reducing the number of bits is adopted.

FIG. 6 illustrates an example of the configuration of the edit table 38 of color data, which is used when the method achieved by reducing the number of bits is adopted. A method for setting the ratio of the color data according to an error rate and a diagnostic mode will be described with reference to FIG. 6.

As illustrated in FIG. 6, the edit table 38 defines how the number of the bits of color data is reduced depending on whether the diagnostic mode is defined to which of "normal mode", "NBI mode", and "ultrasonic mode", with each case of the error rate being "0 percent", "50 percent", and "75 percent", respectively.

For example, it is assumed that the error rate is changed from 0 percent to over 50 percent while an endoscopic image obtained in the normal mode is being transmitted. While the error rate is 0 percent, the ratio of the color data is determined by referring to the first line L1 the first column C1 in the edit table 38. In this case, the number of bits is not reduced, and all (100 percent) bits of luminance Y and color differences Pb and Pr in the bits of the image signal input from the main processor circuit 11 are transmitted. When the error rate becomes over 50 percent, the place to be referred to in the edit table 38 is changed to the second line L2, the first column C1. In this case, the number of the bits of the image signal input from the main processor circuit 11 is reduced. The bits of luminance Y is reduced to 80 percent, and the bits of a color difference Pb and a color difference Pr are reduced to 25 percent and 45 percent, respectively.

The other diagnostic modes or different error rates are handled in a similar manner to the above. Relevant lines L1-L3 and columns C1-C3 on the edit table 38 are referred to, and the numbers of the bits of luminance Y and color differences Pb and Pr are reduced at the rate defined in each place to be referred to.

In the edit table 38 that is illustrated in FIG. 6 as an example, an appropriate ratio of the color data is set for every diagnostic mode according to the characteristics of an observation image, such that the influence on the image quality of an endoscopic image due to the performed reduction process will be minimized. In particular, in the edit table 38, information that prioritizes information of a plurality of color signals according to a diagnostic mode, i.e., the characteristics of an observation image, is set. For example, it is unlikely that the observation of an ultrasonic image by a user such as an operator is impaired even when a certain amount of the information of color differences Pb and Pr is cut off. This is because images in the ultrasonic mode are basically monochrome images. By contrast, images in the normal mode are basically color images. For this reason, the ratio of the color data is set higher in Pr than in Pb such that Pr information that has a high correlation with red will be transmitted on a priority basis. Accordingly, it becomes unlikely that the observation of an image is impaired. As for images in the NBI mode, the ratio of the color data is set higher in Pb than in Pr such that Pb information that has a high correlation with blue will be transmitted on a priority basis.

Note that FIG. 6 merely illustrates an example of how the ratio between luminance Y and color differences Pb and Pr is set and no limitation is indicated therein. Alternatively, the ratio may be determined appropriately according to the characteristics of images in each diagnostic mode and an error rate.

Note that FIG. 6 illustrates three error rates and three diagnostic modes, but no limitation is indicated therein. In addition of the example illustrated in FIG. 6, the ratio of the color data may be defined for further different error rates, or the ratio of the color data may be defined for other diagnostic modes. It is not necessary for the value of an error rate to be one of 0 percent, 50 percent, and 75 percent, and other values may be set. Further, it is not always necessary to define all the diagnostic modes or error rates of FIG. 6.

As described with reference to FIGS. 2A and 2B, the color data editing unit 37 of the transmission data processing unit 13 edits the color data according to the definition in the edit table 38 of FIG. 6, and passes the edited image signal to the image transmission unit 14. Moreover, the color data editing unit 37 generates format information that indicates at what ratio the color data of an image signal is edited, and passes the generated format information to the image transmission unit 14.

FIGS. 7A and 7B depict an example of the signal that the processor 10 transmits in the case where the color data is edited according to the edit table 38 of FIG. 6. How the processor 10 transfers an image signal and information that indicates how the ratio of the color data of an image signal is edited to the monitor 20 in the case where the ratio of the color data is edited according to the definition in the edit table 38 of FIG. 6 will be specifically described with reference to FIGS. 7A and 7B.

FIG. 7A depicts an example of the signal that is output to the image transmission unit 14 by the transmission data processing unit 13 of the processor 10. Here, examples of the configuration of a signal that corresponds to each error rate when the diagnostic mode is "normal mode" are depicted.

A signal that is transmitted to the monitor 20 via the image transmission unit 14 of the processor 10 includes color data, i.e., an image signal indicating an endoscopic image (this will be referred to as "a"), and a signal of format information indicating the ratio of the color data of an image signal.

An "image signal a" in (1) includes the bits whose number of bits is reduced according to the definition in the edit table 38 of FIG. 6. FIG. 7A depicts the image signal that is edited according to line L1, columns C1-C3 of the edit table 38 of FIG. 6.

When the error rate is 0 percent, 10 bits of luminance Y are included in the image signal a. By contrast, when the error rate is, for example, 50 percent, the bits of luminance Y is reduced to 80 percent. Accordingly, "10 bits*0.80=8 bits" will be included in the image signal a. The cases of the other signals (color difference Pb or Pr) and the other error rate are also depicted in FIG. 7A.

The image signals a that correspond to the error rates when the diagnostic mode is set to the "normal mode" are depicted as examples in (1) of FIGS. 7A and 7B. Also when the diagnostic modes other than the normal mode are adopted, the number of bits is reduced according to the reduction rate defined in each place to be referred to in the edit table 38 of FIG. 6 with reference to the number of bits when the error rate is 0 percent. A known technique in the art is used to reduce the number of bits.

Format information in (2) includes information that indicates how many bits of the luminance Y and color differences Pb and Pr in the image signal a are reduced respectively. For example, when the error rate is 50 percent in the normal mode, the format information includes information indicating that the data where the luminance Y, color difference Pb, and color difference Pr are reduced to 80 percent, 25 percent, and 45 percent, respectively, is transmitted as the image signal a.

The format information is transmitted in a format depicted in FIG. 7B. A value that indicates the diagnostic mode is stored in the front field "Operation Mode". The data lengths of the luminance Y and color differences Pb and Pr are stored in the subsequent fields "Y data length", "Pb data length", and "Pr data length", respectively. In the embodiment, the data length of each color data of the luminance Y and color differences Pb and Pr is represented as percentage of how much bit length is included in the image signal a, where the bit length is 100 percent in the case the error rate is 0 percent and no compression is present.

The format information is transmitted, for example, by using a blanking period of an image frame including the image signal a.

FIG. 8 illustrates an example of the configuration of the edit table 38 of color data, which is used when the method achieved by reducing the number of pixels is adopted. The other method for setting the ratio of the color data according to an error rate and a diagnostic mode will be described with reference to FIG. 8.

Note that FIG. 8 depicts only the edit table 38 related to the normal mode. In the edit table 38 of FIG. 8, the values same as those used for reducing the number of bits in FIG. 6 are set to the ratios at which color data with each error rate is compressed. Although the depiction is omitted in FIG. 8, in the embodiment, in a similar manner to the above, color data is compressed at the ratios whose values are same as those used for reducing the number of bits with each error rate in FIG. 6 when the other diagnostic modes are adopted.

In the method achieved by reducing the number of pixels, a specified number of pixels defined by the edit table 38 from among pixels constituting each image frame are not transmitted, thereby reducing the color data of pixels constituting each image frame to a specified rate.

According to the edit table 38 of FIG. 8, whether or not to transmit color data (luminance Y, color differences Pb and Pr) is determined according to the pixel number of a pixel included in each image frame. Among pixels with pixel numbers 1-20 in FIG. 8, pixels whose color data is transmitted to the monitor 20 are indicated with luminance Y and color differences Pb and Pr. Data with a pixel number with no indication of a reference sign (Y, Pb, or Pr) in the edit table 38 is to be deleted in the color data editing unit 37, and is not to be transmitted to the monitor 20. For example, when the error rate is 75 percent, the information of a pixel with pixel number 2 is not transmitted to the monitor 20, and only the information of luminance Y of a pixel is transmitted to the monitor 20 in regard to the pixel information with pixel number 3.

For example, it is configured such that one pixel out of five pixels of luminance Y will not be transmitted to the monitor when the error rate is 50 percent in the normal mode. Accordingly, 80 percent color data of luminance Y is transmitted. In a similar manner, it is configured such that three pixels out of four pixels of color difference Pb will not be transmitted to the monitor 20 when the error rate is 50 percent. Accordingly, percent color data of color difference Pb is transmitted.

FIG. 8 illustrates an example of how the number of pixels is reduced. Whether or not to transmit which of luminance Y, and color differences Pb and Pr of what pixel may be determined without any limitation as long as specified rates (for example, when the error rate is 50 percent in the normal mode, luminance Y, a color difference Pb, and a color difference Pr are reduced to 80 percent, 25 percent, and 45 percent, respectively) are satisfied.

In a similar manner to the edit table of FIG. 6 where the number of bits is reduced, any number of diagnostic modes or error rates may be defined in the edit table 38 where the number of pixels is reduced. Moreover, which diagnostic mode is to be defined, what value is to be set to the value of an error rate or the like may be determined without limitation.

FIGS. 9A and 9B depict an example of the signal that the processor 10 transmits in the case where the color data is edited according to the edit table 38 of FIG. 8. How the processor 10 transfers an image signal and information that indicates how the ratio of the color data of an image signal is edited to the monitor 20 in the case where the ratio of the color data is edited according to the definition in the edit table 38 of FIG. 8 will be specifically described with reference to FIGS. 9A and 9B. Here, differences from an example of the signal described above with reference to FIGS. 7A and 7B will be mainly described.

FIG. 9A depicts an example of the signal that is output to the image transmission unit 14 by the transmission data processing unit 13 of the processor 10. Here, examples of the configuration of a signal that corresponds to each error rate when the diagnostic mode is "normal mode" are depicted.

In a similar manner to the above method achieved by reducing the number of bits, a signal to be transmitted to the monitor 20 in the method achieved by reducing the number of pixels also includes an image signal (this will be referred to as "b") and a signal of format information.

The color data with specified pixel numbers is reduced in the image signal b of (1) according to the edit table 38 of FIG. 8. Information similar to that of FIG. 7A is stored as (2) format information. As depicted in FIG. 9B the format of format information is similar to the format of FIG. 7B where the method achieved by reducing the number of bits is adopted, and a value that indicates the diagnostic mode, and the data length of the luminance Y and color differences Pb and Pr are stored therein in the order from the front field. Here, the data length of the luminance Y and color differences Pb and Pr is represented as percentage of how much pixel from among pixels that constitutes a single image frame is included in the image signal b.

When a signal as depicted in FIGS. 7A and 7B or FIGS. 9A and 9B is received, the monitor 20 uses the radio communication management unit 64 of the image reception unit 21 to determine how much luminance Y and color differences Pb and Pr are reduced according to the received format information. Then, the radio communication management unit 64 of the image reception unit 21 interpolates the bits or pixels reduced from the image signals a and b according to a rate at which the luminance Y and color differences Pb and Pr are reduced, and displays the obtained image signal on a screen.

FIG. 10 depicts processes in which color data of the signal received from the processor 10 is interpolated by the radio communication management unit 64 of the monitor 20 and the signal is output. The columns of FIG. 10 indicates (1) the image signal a or b that is input to the radio communication management unit 64 of the monitor 20, (2) the format information that is input to the radio communication management unit 64, and (3) the output format information that is generated by the radio communication management unit 64, respectively.

As illustrated in FIG. 10, even when the monitor 20 has not received a complete image signal as the number of bits or pixels are reduced due to the deterioration of a communication state, the radio communication management unit 64 interpolates image signal a or b in (1) according to the format information (2) received from the processor 10, and edits the image signal so as to be in an image format that can be processed by the main monitor circuit 23 of FIG. 3. Output format information in (3) is obtained by performing an interpolation process as necessary. For example, in the case where the number of bits is reduced, the removed bits are filled with "0". In the case where the number of pixels is reduced, an interpolation process, for example, a process in which the previous pixel is copied or the removed pixel is filled with a specific value (for example, "0"), is performed appropriately.

In the description above, cases in which the diagnostic mode is set by a user such as an operator via the operation unit 12 of FIGS. 2A and 2B are mainly described, but no limitation is indicated. As described above with reference to FIGS. 2A and 2B, the diagnostic mode may be recognized by analyzing the color information of the image input from the main processor circuit 11 by the automatic image detection unit 31 of the transmission data processing unit 13.

FIG. 11 depicts how the automatic image detection unit 31 recognizes the diagnostic mode from the color information of image.

As illustrated in FIG. 11, the automatic image detection unit 31 may determine that the diagnostic mode is the NBI mode when the color component of a color difference Pb is N or more times greater than the color component of a color difference Pr. The automatic image detection unit 31 may determine that the diagnostic mode is the ultrasonic mode when the color information does not include any component of the color differences Pb and Pr. In the embodiment, the automatic image detection unit 31 determines that the diagnostic mode is the normal mode when the diagnostic mode is neither the NBI mode nor the ultrasonic mode.

When the diagnostic mode is detected by analyzing the color information of image according to the trigger conditions of FIG. 11, as previously described with reference to FIGS. 2A and 2B, it is desired that a chattering control be performed by using the timer 32 such that a diagnostic mode will not be frequently changed.

Next, the flow of a color data editing process performed by the color data editing unit 37 of the transmission data processing unit 13 will be described with reference to a flowchart.

FIG. 12 is a flowchart of a color data editing process performed by the color data editing unit 37 of the processor 10 according to the present embodiment. When a radio communication starts between the processor 10 and the monitor 20 and image is input from the main processor circuit 11 to the transmission data processing unit 13, the color data editing unit 37 starts performing a series of processes of FIG. 12.

Firstly, in step S1, the diagnostic mode stored in the memory 17 is read via the mode setting unit 16.

In step S2, whether or not the set diagnostic mode has been changed by the operation unit 12 is determined. The determination in step S2 is made, for example, depending on whether or not the diagnostic mode stored in the memory 36 or the like of the transmission data processing unit 13 matches the diagnostic mode read in step S1. When the diagnostic mode has not been changed, the color data is edited as necessary according to the method defined in a predetermined place to be referred to in the edit table 38, and the process shifts to step S5. When the diagnostic mode has been changed, the process shifts to step S3.

In step S3, various settings are changed according to the diagnostic mode read in step S1. In particular, the diagnostic mode read in step S1 is written into the memory 36 or the like of the transmission data processing unit 13, and the places to be referred to are changed in the edit table 38.

In step S4, information is read from relevant places of the changed edit table 38, and the color data is edited accordingly. Then, the process shifts to step S5.

In step S5, an error rate is read from the memory 36.

In step S6, whether or not there has been a change in the error rate is determined. The determination in step S6 is made depending on whether or not the read error rate is greater (or less) than a threshold, where the value of an error rate set to the edit table 38 is the threshold. The of the latest error rate notified by the error rate detection unit 15 is held in the memory 36. When the error rate has not been changed, an image signal including the color data is output to the image transmission unit 14, and the process returns to step S1. When the error rate has been changed, the process shifts to step S7.

In step S7, places to be referred to are changed in the edit table 38.

In step S8, information is read from relevant places of the edit table 38, and the color data is edited accordingly. Then, an image signal including the color data is output to the image transmission unit 14, and the process returns to step S1.

As illustrated in FIG. 12, the color data editing unit 37 changes the place to be referred to in the edit table 38 when the set diagnostic mode has been changed or when the notified error rate provided by the monitor 20 has been changed to a degree greater than a specified threshold. Then, the color data will be edited according to the method defined in the changed place to be referred to.

Note that processes in cases where automatic detection of a diagnostic mode is not performed by the automatic image detection unit 31 are illustrated in FIG. 12. In cases where a diagnostic mode is detected the automatic image detection unit 31, the color data editing unit 37 is notified of a diagnostic mode by the automatic image detection unit 31 in step S1 of FIG. 12, and a process of shifting to step S2 is performed in a similar manner to the method described above.

Figure 13A:
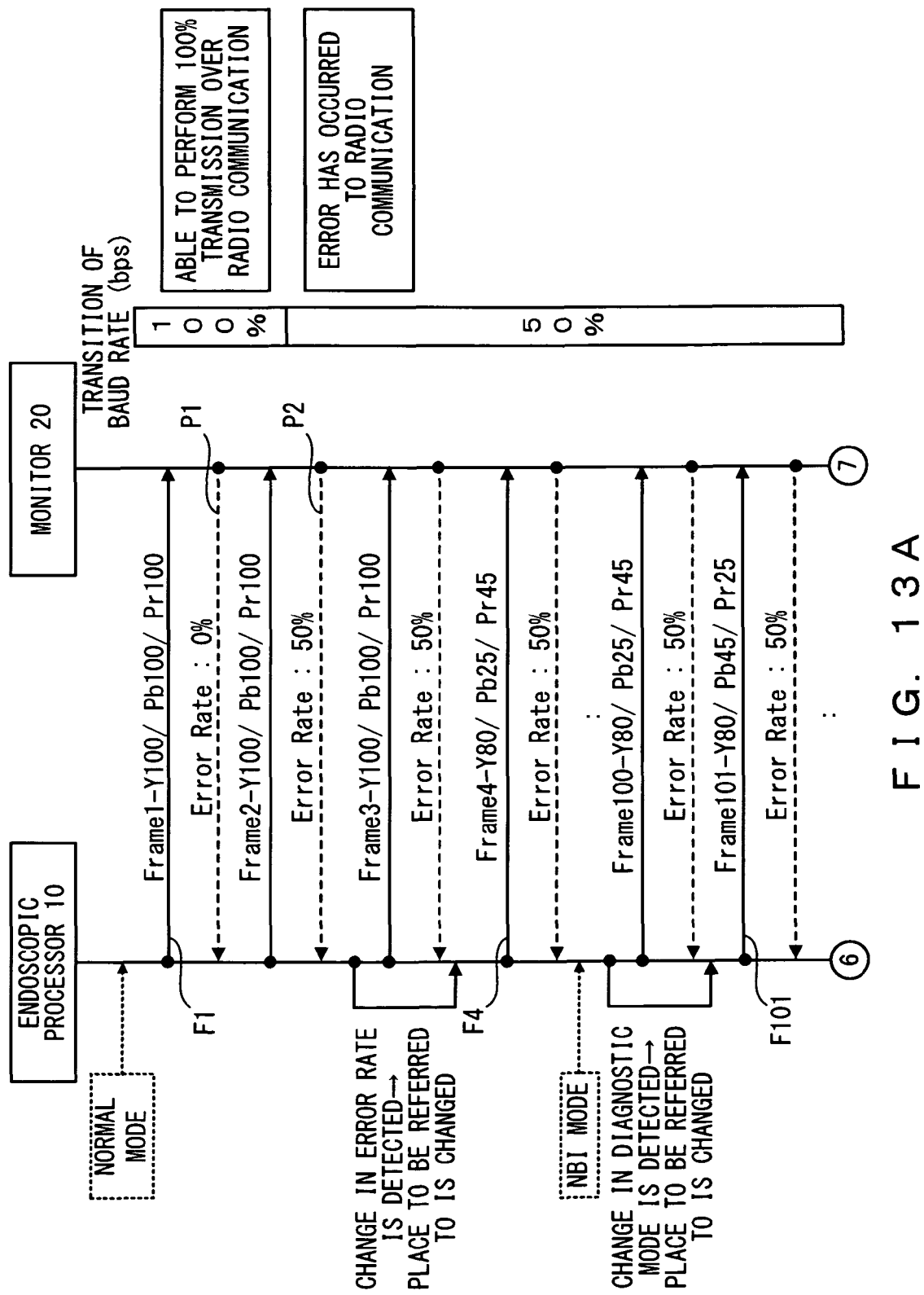
FIG. 13A illustrates specific examples of the sequences (part 1) in which an endoscopic image is exchanged between a processor and a monitor.
Figure 13B:
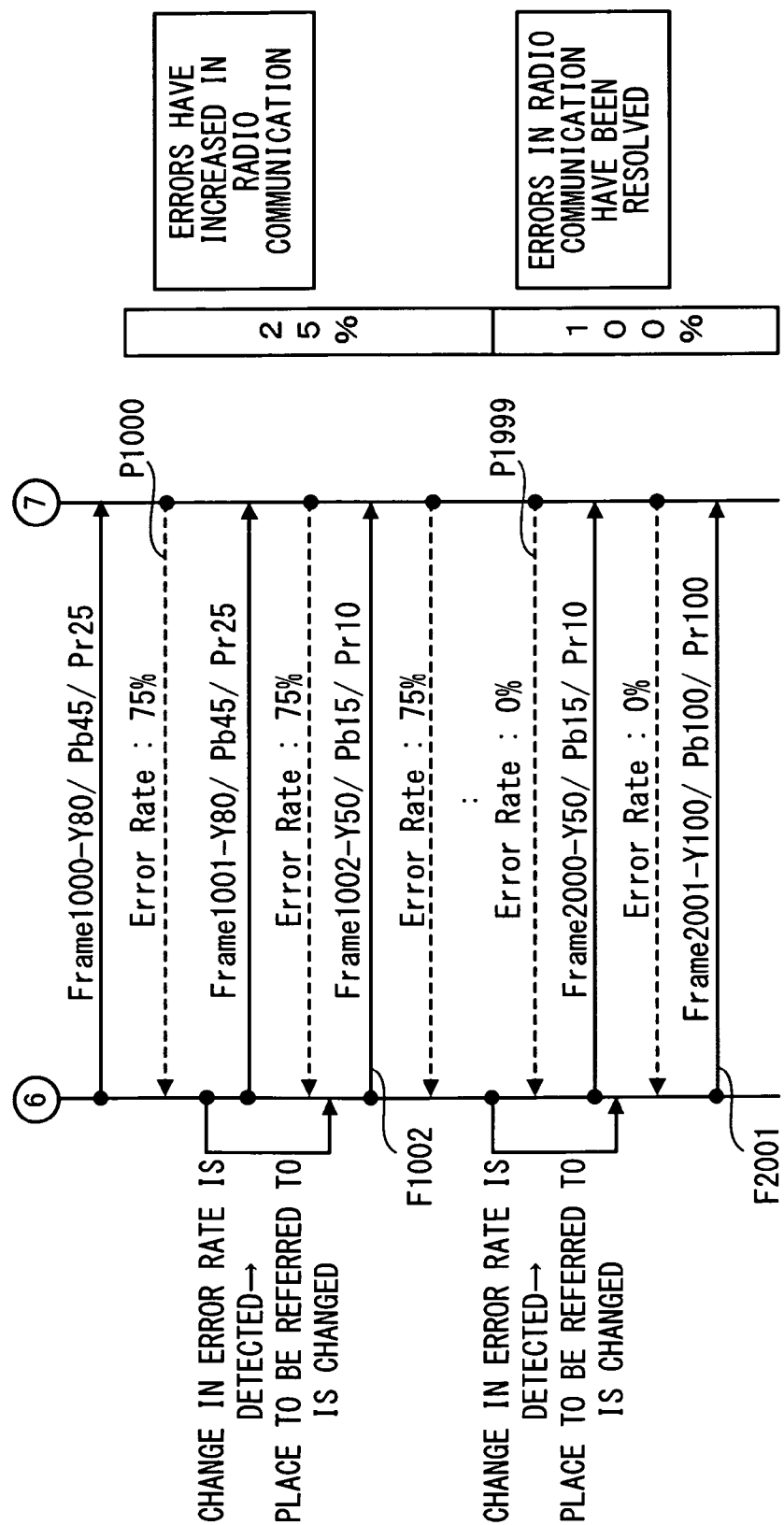
FIG. 13B illustrates specific examples of the sequences (part 2) in which an endoscopic image is exchanged between a processor and a monitor.

FIGS. 13A and 13B illustrate specific examples of the sequences in which an endoscopic image is exchanged between the processor 10 and the monitor 20 by using the methods as above. The processor 10 transmits an image signal at a specified frame rate. It is assumed that the diagnostic mode is set to the "normal mode" when the transmission starts. In a frame F1 at the time when the transmission of a frame starts, compression of color data or the like is not performed, and 100 percent color data is transmitted. In FIGS. 13A and 13B, a frame with frame number N (N=1, 2, . . . ) is represented as "frame FN".

When the communication between the processor 10 and the monitor 20 starts, the transmission rate is 100 percent. Thus, the monitor 20 notifies the processor 10 of the fact that the error rate is 0 percent by using a packet P1 or the like. In FIGS. 13A and 13B, the packet that the monitor 20 returns to the processor 10 in response to a frame with frame number N is represented as "packet PN".

It is assumed that the transmission rate has dropped to 50 percent due to an error or the like occurred to the radio communication while communication is being performed in the normal mode. After the transmission rate has dropped to 50 percent, the monitor 20 will provide a packet P2 and the following packets with notification that the error rate is 50 percent.

When the packet P2 is received, the processor 10 determines that the error rate has become greater than the first threshold (50 percent), and changes the place to be referred to in the edit table 38. After the place to be referred to has been changed, a frame F4 and the following frames are transmitted, for example, upon compressing luminance Y, a color difference Pb, and a color difference Pr to 80 percent, 25 percent, and 45 percent, respectively. While the transmission rate is 50 percent, the monitor 20 similarly responds to the frames that have received the notification that the error rate is 50 percent.

If the diagnostic mode is changed to the NBI mode, the processor 10 changes the place to be referred to in the edit table 38. After the place to be referred to has been changed, a frame F101 and the following frames are transmitted, for example, upon compressing luminance Y, a color difference Pb, and a color difference Pr to 80 percent, 45 percent, and 25 percent, respectively.

Further, it is assumed that errors have increased in the radio communication and the transmission capacity has dropped to 25 percent. In such cases, the monitor 20 will provide notification that the error rate is 75 percent with a packet P1000 and the following packets.

When the packet P1000 is received, the processor 10 determines that the error rate has become greater than the second threshold (75 percent), and changes the place to be referred to in the edit table 38. After the place to be referred to has been changed, a frame F1002 and the following frames are transmitted, for example, upon compressing luminance Y, a color difference Pb, and a color difference Pr to 50 percent, 15 percent, and 10 percent, respectively.

When the errors in the radio communication have been resolved and the transmission rate has recovered to 100 percent afterward, the monitor 20 will provide notification that the error rate is 0 percent with a packet P1999 and the following packets.

When the packet P1999 is received, the processor 10 determines that the error rate has become less than the first and second thresholds, and changes the place to be referred to in the edit table 38. After the place to be referred to has been changed, a frame F2001 and the following frames are transmitted, for example, with luminance Y, a color difference Pb, and a color difference Pr just as they are (without compression).

As described above, according to the wireless image transmission system 100 of the present embodiment, when the communication state is changed while an image signal is being transmitted in the radio communication, the color data editing unit 37 of the transmission data processing unit 13 reduces the amount of color data to be transmitted in accordance with an error rate and a diagnostic mode to maintain the communication. When the error rate becomes high and the traffic is reduced, the compression rate of color data is set so as to minimize the influence on the image quality according to a diagnostic mode, i.e., according to the characteristics of an endoscopic image. Accordingly, sufficient image quality is secured for the endoscopic image displayed on the monitor 20 when a user such as an operator of the wireless image transmission system 100 performs an endoscopic observation or the like.

In addition the above, various applications and modifications may be made to the present invention without departing from the spirit or scope of the present invention. For example, some elements may be deleted from the overall configuration which has been described above in the embodiments. Further, some elements of different embodiments may be combined as necessary.

What is claimed is:

1. A color signal transmission device comprising:
a processor configured to:
generate a first color signal from among a plurality of color signals for creating an image;
generate a second color signal from among a plurality of color signals for creating an image;
select either a first diagnostic mode for creating a first diagnostic image by using the first color signal and the second color signal, or a second diagnostic mode for creating a second diagnostic image that is different from the first diagnostic mode;

prioritize information relating to the first color signal and the second color signal generated by the processor, according to a diagnostic mode selected by the processor;
change transmission rates of the first color signal and the second color signal generated by the processor, according to a priority determined by the processor; and
transmit the first color signal and the second color signal according to the changed transmission rates; wherein
when a special light mode, in which endoscopy with special light is performed, is selected by the processor, the processor changes the transmission rates of the first color signal and the second color signal such that a value of a color difference Pb in a ratio of the color difference Pb to a color difference Pr becomes higher than a value of a color difference Pr in the image signal.

2. A color signal transmission device comprising:
a processor configured to:
generate a first color signal from among a plurality of color signals for creating an image;
generate a second color signal from among a plurality of color signals for creating an image;
select either a first diagnostic mode for creating a first diagnostic image by using the first color signal and the second color signal, or a second diagnostic mode for creating a second diagnostic image that is different from the first diagnostic mode;
prioritize information relating to the first color signal and the second color signal generated by the processor, according to a diagnostic mode selected by the processor;
change transmission rates of the first color signal generated by the processor and the second color signal generated by the processor, according to a priority determined processor; and
transmit the first color signal and the second color signal according to the changed transmission rates; wherein
when an ultrasonic mode, in which endoscopy with ultrasonic waves is performed, is selected by the processor, the processor changes the transmission rates of the first color signal and the second color signal such that a value of a luminance Y in the image signal is increased.

3. A transmitter used in a wireless image transmission system that transmits and receives, by radio communication, an image signal obtained by converting an image that is obtained by an endoscope apparatus, the transmitter comprising:
a processor configured to:
monitor a communication state of radio communication;
edit the image signal according to a mode in which the endoscope apparatus obtains an image when a change in a communication state is detected by the processor;
transmit the image signal output from the processor to a receiver;
determine a mode of the endoscope apparatus from among the following modes: (1) a normal mode in which normal endoscopy is performed; (2) a special light mode in which endoscopy with special light is performed; and (3) an ultrasonic mode in which endoscopy with ultrasonic waves is performed; and
store color data reduction rate information in each of the normal mode, the special light mode, and the ultrasonic mode, wherein
when the image signal is to be edited, the processor obtains color data reduction rate information that corresponds to the mode determined by the processor, and edits a value of color data according to the obtained color data reduction rate information, and
when the processor detects deterioration in a communication state and the mode is the special light mode, the processor edits the image signal such that a value of a color difference Pb in a ratio of the color difference Pb to a color difference Pr becomes higher than a value of a color difference Pr in the image signal.

4. The transmitter according to claim 3, wherein when deterioration in a communication state is detected by the processor and the mode is the normal mode, the processor edits the image signal such that the value of the color difference Pr in the ratio of the color difference Pb to the color difference Pr becomes higher than the value of the color difference Pb.

5. The transmitter according to claim 4, wherein when deterioration in a communication state is detected by the processor and the mode is the normal mode, the processor edits the image signal such that the value of the color difference Pr in a ratio of the color difference Pb to the color difference Pr becomes higher than the value of the color difference Pb.

6. A transmitter used in a wireless image transmission system that transmits and receives, by radio communication, an image signal obtained by converting an image that is obtained by an endoscope apparatus, the transmitter comprising a processor configured to:
monitor a communication state of radio communication;
edit the image signal according to a mode in which the endoscope apparatus obtains an image when a change in a communication state is detected by the processor;
to transmit the image signal output from the processor to a receiver;
determine a mode of the endoscope apparatus from among the following modes: (1) a normal mode in which normal endoscopy is performed; (2) a special light mode in which endoscopy with special light is performed; and (3) an ultrasonic mode in which endoscopy with ultrasonic waves is performed; and
store color data reduction rate information in each of the normal mode, the special light mode, and the ultrasonic mode, wherein
when the image signal is to be edited, the processor obtains color data reduction rate information that corresponds to the mode determined by the processor, and edits a value of color data according to the obtained color data reduction rate information, and
when the processor detects deterioration in a communication state and the mode is the ultrasonic mode, the processor edits the image signal such that a value of a luminance Y in the image signal is increased.

7. A wireless image transmission system including a transmitter to transmit, by radio communication, an image signal obtained by converting an image that is obtained by an endoscope apparatus, and a receiver having a display unit on which the image signal received from the transmitter is displayed,
the transmitter comprising a processor configured to:
monitor a communication state of radio communication;
edit the image signal according to a mode in which the endoscope apparatus obtains an image when a change in a communication state is detected by the processor;
transmit the image signal output from the processor to a receiver;

determine a mode of the endoscope apparatus from among the following modes: (1) a normal mode in which normal endoscopy is performed; (2) a special light mode in which endoscopy with special light is performed; and (3) an ultrasonic mode in which endoscopy with ultrasonic waves is performed; and store color data reduction rate information in each of the normal mode, the special light mode, and the ultrasonic mode, and the receiver comprising:

an analysis unit to edit an image signal received from the transmitter into a format enabling the image signal to be displayed on the display unit, and to detect a communication state, wherein when the image signal is to be edited, the processor obtains color data reduction rate information that corresponds to the mode determined by the processor, and edits a value of color data according to the obtained color data reduction rate information, and when the processor detects deterioration in a communication state and the mode is the special light mode, the processor edits the image signal such that a value of a color difference Pb in a ratio of the color difference Pb to a color difference Pr becomes higher than a value of a color difference Pr in the image signal.

8. A wireless image transmission system including a transmitter to transmit, by radio communication, an image signal obtained by converting an image that is obtained by an endoscope apparatus, and a receiver having a display unit on which the image signal received from the transmitter is displayed, the transmitter comprising a processor configured to:

monitor a communication state of radio communication;

edit the image signal according to a mode in which the endoscope apparatus obtains an image when a change in a communication state is detected by the processor;

transmit the image signal output from the processor to a receiver;

determine a mode of the endoscope apparatus from among the following modes: (1) a normal mode in which normal endoscopy is performed; (2) a special light mode in which endoscopy with special light is performed; and (3) an ultrasonic mode in which endoscopy with ultrasonic waves is performed; and store color data reduction rate information in each of the normal mode, the special light mode, and the ultrasonic mode, and the receiver comprising:

an analysis unit to edit an image signal received from the transmitter into a format enabling the image signal to be displayed on the display unit, and to detect a communication state, wherein when the image signal is to be edited, the processor obtains color data reduction rate information that corresponds to the mode determined by the processor, and edits a value of color data according to the obtained color data reduction rate information, and when the processor detects deterioration in a communication state and the mode is the ultrasonic mode, the processor edits the image signal such that a value of a luminance Y in the image signal is increased.

* * * * *